(12) United States Patent
Noone

(10) Patent No.: US 7,909,810 B2
(45) Date of Patent: Mar. 22, 2011

(54) GUIDING CATHETER WITH RESILIENTLY COMPRESSIBLE OCCLUDER

(75) Inventor: Michael S. Noone, Londonderry, NH (US)

(73) Assignee: Medtronic Vascular, Inc, Santa Rosa, CA (US)

(*) Notice: Subject to any disclaimer, the term of this patent is extended or adjusted under 35 U.S.C. 154(b) by 185 days.

(21) Appl. No.: 12/325,547

(22) Filed: Dec. 1, 2008

(65) Prior Publication Data
US 2009/0137982 A1    May 28, 2009

Related U.S. Application Data

(62) Division of application No. 11/111,394, filed on Apr. 21, 2005, now abandoned.

(51) Int. Cl.
*A61M 31/00* (2006.01)
*A61M 29/00* (2006.01)

(52) U.S. Cl. .................................. 604/509; 604/104

(58) Field of Classification Search ............ 604/103.03, 604/104, 105, 509, 510; 606/191
See application file for complete search history.

(56) References Cited

U.S. PATENT DOCUMENTS

| | | | |
|---|---|---|---|
| 3,565,079 A | 2/1971 | Jackson | |
| 3,640,282 A | 2/1972 | Kamen | |
| 3,915,171 A | 10/1975 | Shermeta | |
| 3,971,385 A | 7/1976 | Corbett | |
| 4,531,943 A | 7/1985 | Van Tassel et al. | |
| 5,333,614 A * | 8/1994 | Feiring ................. | 600/466 |
| 5,395,330 A | 3/1995 | Marcadis et al. | |
| 5,695,457 A * | 12/1997 | St. Goar et al. ........... | 604/4.01 |
| 6,312,407 B1 | 11/2001 | Zando-Azizi et al. | |
| 6,428,502 B1 | 8/2002 | Lang | |
| 6,595,952 B2 | 7/2003 | Forsberg | |
| 6,650,923 B1 | 11/2003 | Lesh et al. | |
| 2002/0052638 A1 | 5/2002 | Zadno-Azizi | |

FOREIGN PATENT DOCUMENTS
WO    WO2004006804    1/2004

* cited by examiner

*Primary Examiner* — Nicholas D Lucchesi
*Assistant Examiner* — Nathan R Price

(57) ABSTRACT

A guiding catheter for providing proximal occlusion while intubating a branch vessel lumen in a patient. The catheter comprises an elongate hollow shaft having open proximal and distal ends and a resiliently compressible occluder fixed about the shaft adjacent the distal end, the occluder having a relaxed shape that tapers distally from a major diameter greater than a diameter of the vessel lumen. The occluder may comprise elastic foam material or an impermeable flexible cover clingingly enclosing a resilient support member.

6 Claims, 3 Drawing Sheets

GUIDING CATHETER WITH RESILIENTLY COMPRESSIBLE OCCLUDER

CROSS-REFERENCE TO RELATED APPLICATIONS

This is a division of U.S. patent application Ser. No. 11/111,394, filed Apr. 21, 2005, now abandoned.

FIELD OF THE INVENTION

The present invention relates generally to an intraluminal guiding catheter used for intubation of a branch vessel, and more particularly, to a guiding catheter with a resiliently compressible occluder disposed adjacent the distal end of the catheter.

BACKGROUND OF THE INVENTION

Stenotic lesions form on the lumen walls of blood vessels to create narrowings that restrict blood flow through the vessel, and may comprise a hard, calcified substance and/or a softer thrombus material. Interventional catheterization procedures such as balloon angioplasty, stent deployment, atherectomy, and thrombectomy are well known and have proven effective in the treatment of such stenotic lesions. Such modalities require the passage of a therapy catheter through a patient's vasculature and into a targeted branch vessel.

Recently, a variety of devices have been developed to address atheroembolization, which is the obstruction of blood vessels by stenotic debris released during interventional catheterization therapies such as those mentioned above. Distal protection devices (DPDs) such as filters and occluders represent one class of intravascular devices that can be used to prevent atheroembolization. A filter mounted on a guidewire or a catheter may be positioned distally of a stenosis to capture and remove potentially embolic debris without causing hemostasis during use of the filter. Alternatively, an occluder device may be positioned distally of a stenosis to temporarily stop the flow of blood, including any stenotic debris that may have become entrained in the blood. The contaminated blood is aspirated from the treated area before the distal occluder device is collapsed to permit resumption of blood flow.

Occlusion devices may also be placed proximally of a stenosis to provide so-called proximal protection. Proximal occlusion devices may be used alone to prevent atheroembolization, or they may be used in conjunction with a distal occluder to form an isolated treatment chamber about the stenosis to be treated. Preliminary deployment of a proximal occlusion device may be advantageous in preventing atheroembolization because advancing a treatment catheter, a guidewire or a DPD into a stenosis can dislodge particulate debris, even before the stenosis is being opened. Proximal occlusion can create temporary hemostasis in the vessel to prevent distal embolization by debris created during crossing and/or treatment of the lesion. As is done with distal occlusion, contaminated blood is aspirated from the treated area before the proximal occluder device is collapsed to permit resumption of blood flow.

Known occluder devices typically employ an inflatable occlusion balloon or a mechanically expandable occluder element with their attendant expansion apparatuses. For a proximal occlusion device such as a guiding catheter, an occlusion balloon requires an inflation lumen extending around or alongside a main lumen to provide fluid actuation of the balloon from the proximal end of the catheter. A guiding catheter having a mechanically expandable occluder typically requires a slidable sleeve or push/pull wire for mechanical actuation of the occluder from the proximal end of the catheter. Adding an extra lumen or additional actuator features to a guiding catheter disadvantageously require the outside diameter to be larger, and/or the inside diameter of the main lumen to be smaller. Thus, a need exists for a guiding catheter having an atheroembolization prevention system that does not require increasing the wall thickness of the guiding catheter. Such a guiding catheter should be operable simply and quickly during interventional catheterization procedures. Other desirable features and characteristics of the present invention will become apparent from the subsequent detailed description and the appended claims taken in conjunction with the accompanying drawings.

BRIEF SUMMARY OF THE INVENTION

The present invention pertains to a guiding catheter for providing proximal occlusion while intubating a branch vessel lumen in a patient. The catheter comprises an elongate hollow shaft having open proximal and distal ends and a resiliently compressible occluder fixed about the shaft adjacent the distal end, the occluder having a relaxed size and shape that tapers distally from a major diameter greater than a diameter of the vessel lumen. The occluder does not require any type of actuation from the proximal end of the catheter. The occluder may comprise elastic foam material or a resilient support member clingingly enclosed by an impermeable flexible cover.

A method is also disclosed for using the inventive guiding catheter. The method includes providing a guiding catheter having one of the embodiments described above, compressing the resilient occluder while inserting the guiding catheter into the vascular system of the patient, advancing the catheter shaft distal end to a branch vessel in the patient, and intubating the vessel with the catheter shaft distal end such that the occluder is wedged into the vessel lumen until the major diameter of the occluder passes beyond a vessel origin and into sealing engagement with a wall of the vessel lumen to provide occlusion of blood flowing there through.

In other embodiments of the invention, the method may also include inserting a therapeutic device through the guiding catheter, and operating the therapeutic device to treat the patient from within the targeted branch vessel.

BRIEF DESCRIPTION OF THE DRAWINGS

The following drawings are illustrative of particular embodiments of the invention and therefore do not limit its scope. They are presented to assist in providing a proper understanding of the invention. The drawings are not to scale and are intended for use in conjunction with the explanations in the following detailed descriptions. Like reference numerals denote like elements in the drawings, wherein.

DETAILED DESCRIPTION OF A PREFERRED EMBODIMENT OF THE INVENTION

The following detailed description is merely exemplary in nature and is not intended to limit the invention or the application and uses of the invention. Although the description of the invention is in the context of protection against atheroembolization during treatment of blood vessels such as the coronary, carotid and renal arteries, the invention may also be used in any other passageways where it is deemed useful to provide temporary occlusion to block fluid flow. Furthermore, there is no intention to be bound by any expressed or implied theory presented in the preceding technical field, background, brief summary or the following detailed description.

Figure 1:
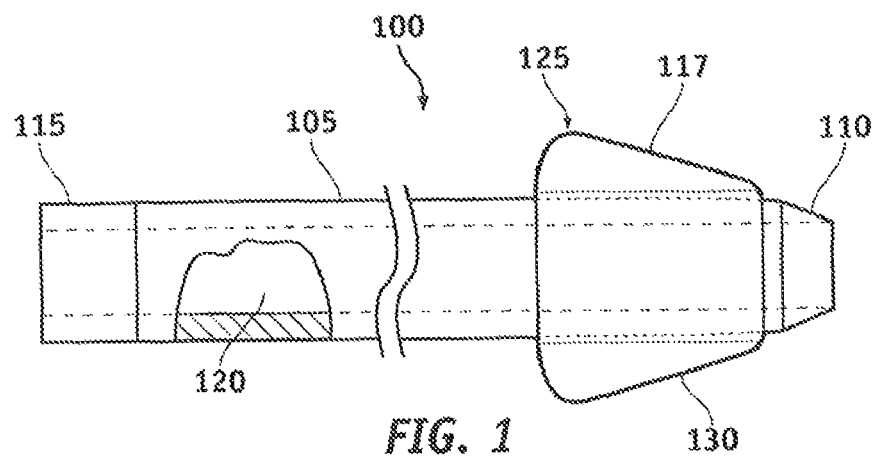
FIG. 1 is a side view of one embodiment of a guiding catheter in accordance with the invention, wherein an occluder is shown in a relaxed configuration.

FIG. 1 illustrates one embodiment of guiding catheter 100, including catheter shaft 105, optional soft tip 110, connector fitting 115 and resiliently compressible occluder 117 shown in a normal, or relaxed, expanded configuration. Lumen 120 extends through shaft 105 between open proximal and distal ends, and is sized and shaped to receive and direct there through a variety of treatment devices such as guidewires and/or therapeutic devices including, but not limited to balloon catheters or stent delivery systems.

Occluder 117 is mounted around catheter shaft 105 adjacent to the distal end thereof, and is made from a resilient, or elastic, biocompatible foam material that is soft enough to be compressed when occluder 117 is wedged into a vessel lumen during intubation by the guiding catheter distal end. Occluder 117 is also soft enough to be compressed as it is wedged into an introducer sheath (see element 460 in FIG. 4) during insertion of catheter 100 into the patient. The elastic foam material comprising occluder 117 may be latex, silicone elastomer, or other viscous forms of natural and synthetic rubbers such as butadiene/acrylonitride copolymers, copolyesters, ethylene vinylacetate (EVA) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, or styrene-ethylene/butylene-styrene. The elastic foam material may be closed-cell or open-cell, although if it is open cell, then means must be provided to seal the porosity of the material so that it can function as an occluder. Flexible cover 235, as will be described further below, may be used to seal an open cell foam occluder.

Occluder 117 has a normal, or relaxed size and shape that, when wedged past an ostium or origin of a branch vessel, will compress to effect sealing engagement with the wall of the vessel lumen. To achieve such a sealing engagement, the relaxed shape of occluder 117 has a diameter at its broadest transverse section, or major diameter 125 that is greater than the diameter of the vessel lumen. To help to prevent injury to the ostium or the wall of the vessel lumen as occluder 117 is wedged into sealing engagement, the relaxed shape of occluder 117 includes taper 130 extending distally from major diameter 125. Taper 130 may be a distal portion of a relaxed shape selected from a variety of possible shapes of occluder 117. Similarly, to help to prevent injury to the ostium or the wall of the vessel lumen as occluder 117 is withdrawn with guiding catheter 100, the relaxed shape of occluder 117 may also include a taper extending proximally from major diameter 125. The distal and proximal tapers may be similar or different, and they may be curved rather than purely conical. For example, the relaxed shape of occluder 117 may be asymmetrically biconical, conical, ellipsoidal, symmetrically biconical, or ovoidal. Occluder 117 may be attached to shaft 105 by any suitable manner known in the art, for example, a biocompatible adhesive such as a cyanoacrylate.

Figure 4:
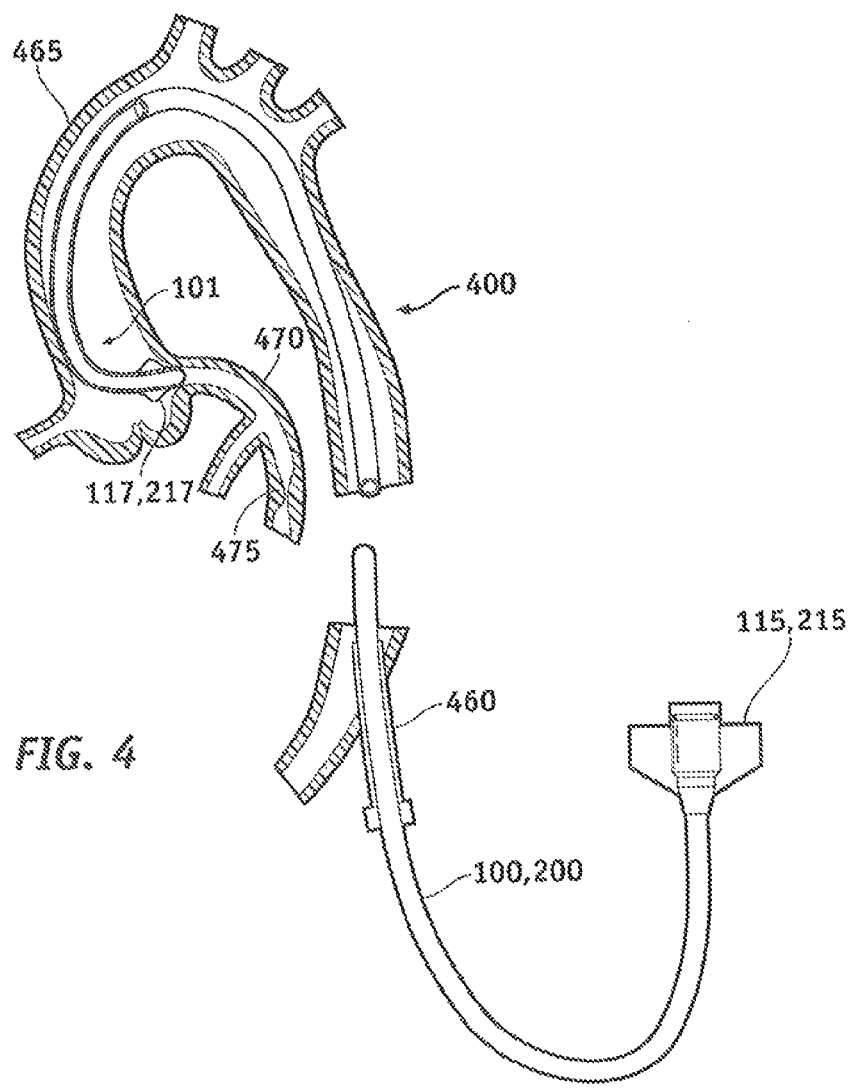
FIG. 4 illustrates one embodiment of a guiding catheter in accordance with the invention, shown deployed in the cardiovascular system of a patient.

Catheter shaft 105 is a flexible shaft that is designed to be advanced through a patient's vasculature to remote arterial locations without buckling or undesirable bending. As shown in FIG. 4, and as is well known to those of skill in the art, catheter shaft 105 may include a pre-formed distal curve 101 that can aid in traversing a patient's vasculature, or can provide enhanced "backup support" as therapeutic catheters are advanced through lumen 120 of guiding catheter 100 and across a stenosis. Any one of a number of pre-formed curvilinear shapes may be incorporated into guiding catheter 100, such as Judkins-type or Amplatz-type curves, as non-limiting examples. Catheter shaft 105 may be constructed of one or more flexible biocompatible materials, including, but not limited to, polyamide, polyester, polyethylene, polyethylene block amide copolymer, polyolefin, polypropylene and polyurethane. Catheter shaft 105 may also include a layer of braided filaments that resists kinking and enhances longitudinal transmission of rotation. To further aid in advancing guiding catheter 100 through the patient's vasculature, it may be desirable to vary the stiffness of catheter shaft 105 by varying the braid pitch, by varying the properties of the materials used in constructing the catheter, or by combining both techniques. The distal end of catheter shaft 105 may include soft tip 110 formed thereon via any of numerous methods known to those skilled in the art.

Connector fitting 115 is coupled to, and provides a functional access port at the proximal end of guiding catheter 100. Connector fitting 115 may be made of metal or of a hard polymer (e.g. medical grade polycarbonate, polyvinyl chloride, acrylic, acrylonitrile butadiene styrene (ABS), or polyamide) that possesses the requisite structural integrity, as is well known to those of skill in the art.

Lumen 120 of guiding catheter 100 may include a slippery interior surface for reducing frictional forces between the interior surface and devices that may be moved through lumen 120. In one exemplary embodiment, the interior surface is provided with a slippery coating, such as a silicone compound or a hydrophilic polymer. In another exemplary embodiment, the interior surface includes a liner formed from a slippery material. Those with skill in the art may appreciate that any one of numerous low-friction, biocompatible materials such as, for example, fluoropolymers (e.g. PTFE, FEP), polyolefins (e.g. polypropylene, high-density polyethylene), or polyamides, may be used for the liner.

Figure 2:
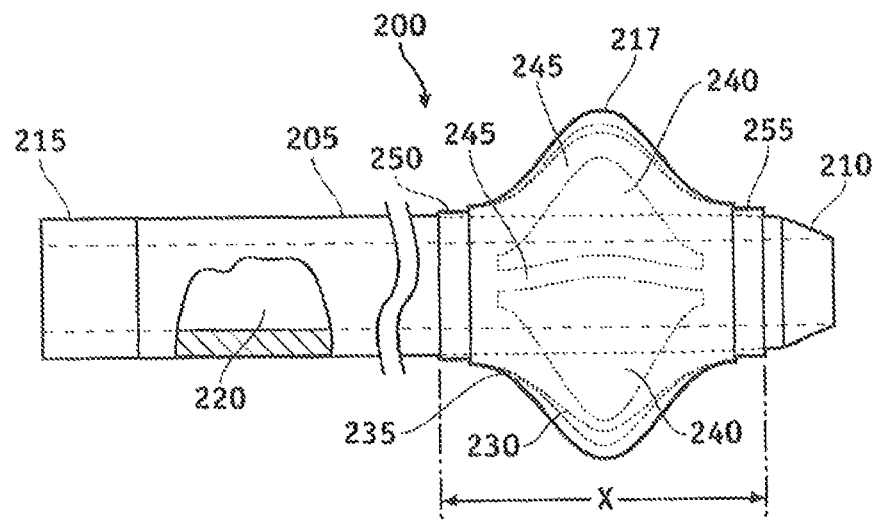
FIG. 2 is a side view of another embodiment of a guiding catheter in accordance with the invention, wherein an alternative occluder is shown in a relaxed configuration.

FIG. 2 illustrates another embodiment of the invention wherein guiding catheter 200 includes catheter shaft 205 (similar to catheter shaft 1105), optional soft tip 210 (similar to soft tip 110), connector fitting 215 (similar to connector fitting 115) and resiliently compressible occluder 217 shown in a normal, or relaxed, expanded configuration. Lumen 220 (similar to lumen 120) extends through shaft 205 between open proximal and distal ends, and is sized and shaped to receive and direct there through a variety of treatment devices such as guidewires and/or therapeutic devices including, but not limited to balloon catheters or stent delivery systems.

Figure 3:
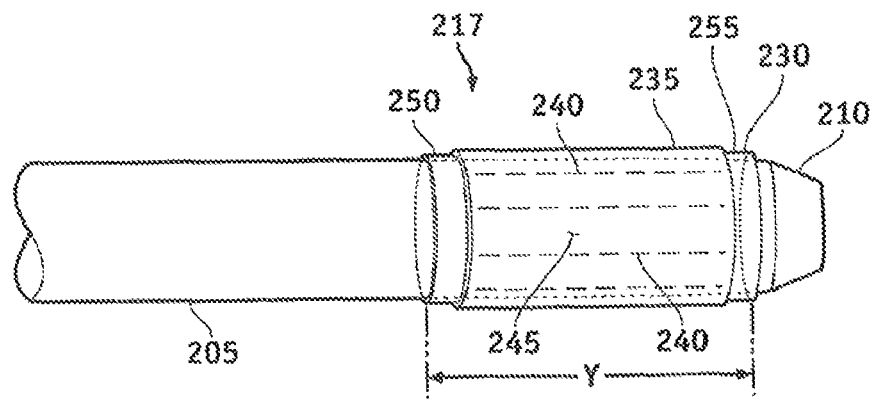
FIG. 3 is a perspective view of a distal portion of the embodiment shown in FIG. 2, wherein the occluder is shown in a compressed configuration.

Occluder 217 is mounted around catheter shaft 205 adjacent the distal end thereof and includes tubular, resilient, support member 230 clingingly encased by impermeable flexible cover 235. FIG. 3 shows resilient occluder 217 in a compressed configuration, as it might appear when wedged into an introducer sheath or into a vessel lumen beyond the ostium thereof. Support member 230 includes proximal and distal ends 250, 255, respectively. A plurality of longitudinal slits 240 extends between proximal and distal ends 250, 255 to generate a plurality of longitudinal struts 245. At least one of support member ends 250, 255 is intact, in that slits 240 do not extend all the way to the end of support member 230. Flexible cover 235 clings to struts 245, spanning the open slits there between to make occluder 217 impermeable to fluid in a patient's vessel. Flexible cover 235 may be formed from an elastic material such as latex, silicone elastomer, or other viscous forms of natural and synthetic rubbers such as butadiene/acrylonitride copolymers, copolyesters, ethylene vinylacetate (EVA) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, and styrene-ethylene/butylene-styrene. Alternatively, flexible cover 235 may be formed from an inelastic material that is thin, flexible and foldable, such as polyamide, polyethylene, polyethylene terephthalate, polyolefin, polypropylene, or polyvinyl chloride.

One of support member ends 250, 255 may be slidably mounted along catheter shaft 205, with the other end being fixed to catheter shaft 205 by any suitable manner known in the art, such as epoxy adhesive or cyanoacrylate. For example, proximal end 250 may be sealingly fixed to shaft 205 and flexible cover 235 may have proximal and distal ends sealingly fixed to support member ends 250, 255, respectively. Alternatively, in an embodiment not shown, the proximal and distal ends of flexible cover 235 may be fixed directly to catheter shaft 205 and both of support member ends 250, 255 may be slidably mounted along catheter shaft 205 within flexible cover 235 between the cover ends. In this alternative example, at least the cover proximal end is sealingly fixed to shaft 205 by a sealed bond joint to prevent fluid flow there through.

In the relaxed, expanded configuration of occluder 217 shown in FIG. 2, support member 230 has a first length X. When struts 245 are radially compressed, support member ends 250 and 255 separate to create a second length Y, as shown in FIG. 3. Second length Y is longer than first length X. As described above, at least one of support member ends 250, 255 slides freely along catheter shaft 205 to accommodate the dimensional changes between lengths X and Y.

Support member 230 may be constructed of a material having sufficient resiliency to recover its original pre-formed shape after struts 245 are temporarily compressed, and also having sufficient resiliency to expand flexible covering 235 therewith. Support member 230 may be made from a high-modulus thermoplastic or thermo-set plastic, nitinol (TiNi), stainless steel or a work-hardenable super alloy comprising nickel, cobalt, chromium and molybdenum. Struts 245 of support member 230 are pre-formed in the relaxed size and shape of occluder 217 by an appropriate process selected from techniques such as casting, heat setting, molding, stamping or thermoforming, depending on the type of material chosen.

A presumptive exemplary method of using guiding catheter 100, 200 will now be described. FIG. 4 illustrates guiding catheter 100, 200 positioned within patient's vascular system 400 for use with a therapeutic device. The clinician manually squeezes resilient occluder 117, 217 to a compressed configuration and inserts the distal end of guiding catheter 100, 200 through introducer sheath 460 into vascular system 400, typically through a femoral artery in the groin area. After exiting introducer sheath 460 into vascular system 400, occluder 117, 217 will resiliently return to its normal expanded size and shape. Guiding catheter 100, 200 is advanced through aorta 465 until the distal end of the catheter is located near the ostium of targeted branch artery 470. In the example shown, branch artery 470 is a patient's left coronary artery.

Figure 5:
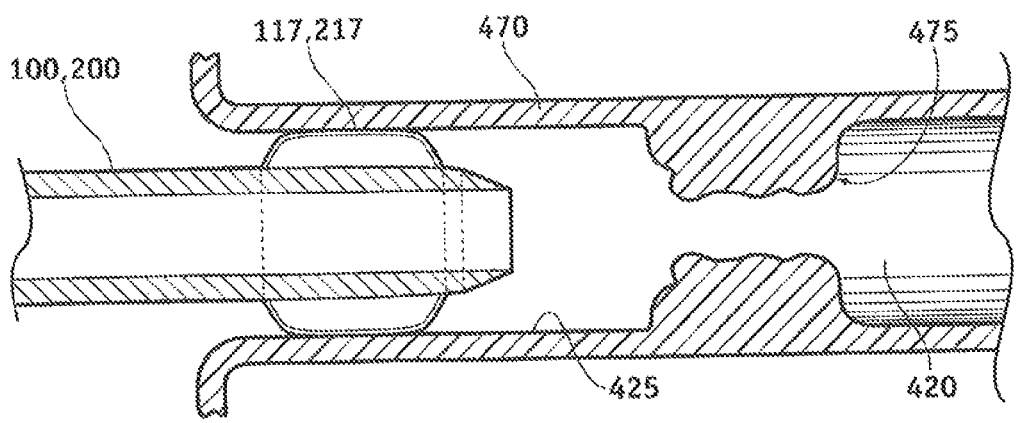
FIGS. 5-8 are longitudinal cross-sectional views that illustrate the use of the inventive guiding catheter in a diseased vessel during an angioplasty procedure.
Figure 6:
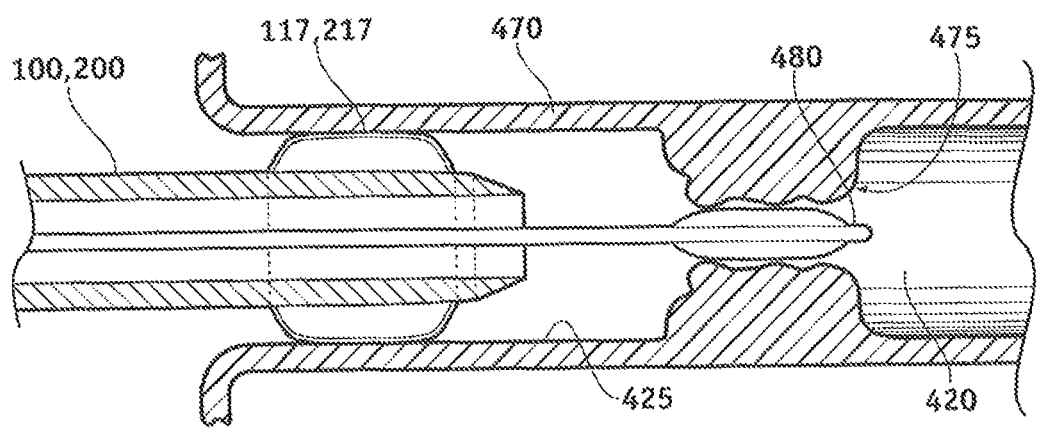
Figure 7:
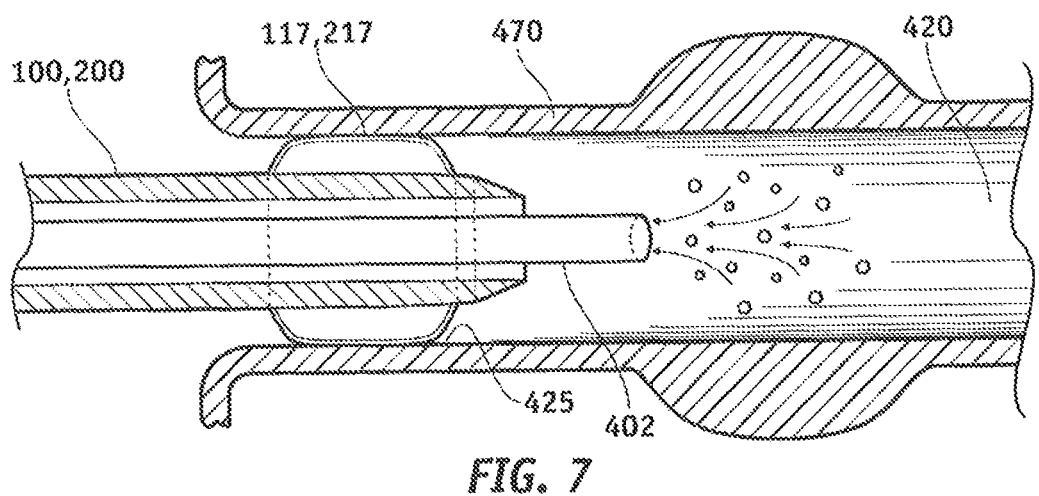
Figure 8:
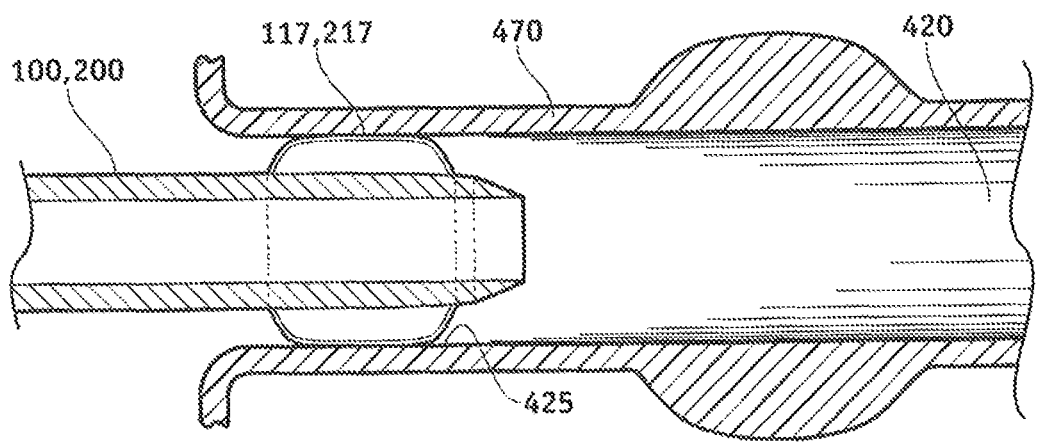

When the distal end of guiding catheter 100, 200 is inserted into the ostium of artery 470, resilient occluder 117, 217 is squeezed, or wedged into sealing engagement with vessel wall 425, thus occluding vessel lumen 420 proximal to stenosis 475, as shown in FIG. 5. Preferably, the distal end of guiding catheter 100, 200 is inserted into artery 470 until major diameter 125 is beyond the ostium to provide optimal sealing between occluder 117, 217 and vessel wall 425. A therapeutic device, such as balloon dilatation catheter 480, including a dilatation balloon, is advanced through central lumen 120, 220 until the balloon reaches a desired position within stenosis 475, as illustrated in FIG. 6. The dilatation balloon is then inflated to dilate stenosis 475. Balloon dilatation catheter 480 may then be removed, and blood may be aspirated from lumen 420, including any debris released during the dilation of stenosis 475. Aspiration may be performed either directly into lumen 120, 220 of guiding catheter 100, 200 or, alternatively, into aspiration catheter 402, which may be advanced to the treated area within vessel lumen 420, as shown in FIG. 7. As will be recognized by those of skill in the art, aspiration during proximal occlusion of an artery requires retrograde blood flow in arterial lumen 420. If retrograde flow through the capillary bed is insufficient to support aspiration of the potentially contaminated blood, then simultaneous flush and aspiration can be established through aspiration catheter 402 and guiding catheter 100, 200. If used, aspiration catheter 402 may be subsequently withdrawn from lumen 120, 220, as shown in FIG. 8. Lastly, guiding catheter 100, 200 is withdrawn from vessel lumen 420.

While at least one exemplary embodiment has been presented in the foregoing detailed description, it should be understood that various changes can be made in the function and arrangement of elements without departing from the scope of the invention as set forth in the appended claims and the legal equivalents thereof.

The invention claimed is:

1. A method of intubating a branch vessel in a patient, the vessel having an ostium, a lumen and a lumen wall, the method comprising the following steps in order:
    receiving a guiding catheter comprising an elongate hollow shaft having open proximal and distal ends and a resiliently compressible occluder sealingly fixed about the shaft adjacent the distal end and having a relaxed size and shape including a major diameter greater than a diameter of the lumen, the shaft lacking structure for fluid or mechanical actuation of the occluder from the shaft proximal end;
    inserting an introducer sheath into a vascular system of the patient;
    manually compressing the occluder into a compressed configuration capable of being inserted into the introducer sheath;
    inserting the catheter shaft distal end through the introducer sheath into the vascular system of the patient until the occluder enters the vascular system and resiliently expands to the relaxed size and shape;
    advancing the catheter shaft distal end to the branch vessel in the patient;
    intubating the vessel with the catheter shaft distal end; and
    wedging the compressible occluder into the vessel lumen such that the major diameter of the occluder passes beyond the vessel ostium to compress the occluder into sealing engagement with the wall of the vessel lumen to provide temporary hemostasis.

2. The method of claim 1 further comprising:

inserting a therapeutic device through the guiding catheter; and operating the therapeutic device to treat the patient from within the branch vessel.

3. The method of claim 2, wherein the therapeutic device is an angioplasty catheter and operating the therapeutic device comprises inflating a balloon to dilate a stenosis in the vessel.

4. The method of claim 2 further comprising:
removing the therapeutic device from the guiding catheter after operating the therapeutic device.

5. The method of claim 4 further comprising:
aspirating blood from the vessel lumen through the guiding catheter.

6. The method of claim 1 wherein a distal region of the shaft is pre-formed into a curvilinear shape.

* * * * *